US010738973B2

(12) United States Patent
Caldwell et al.

(10) Patent No.: US 10,738,973 B2
(45) Date of Patent: Aug. 11, 2020

(54) DEVICE FOR THE SPHERICAL ORIENTATION OF AN OPTICAL ELEMENT, IN PARTICULAR FOR DIRECTING A LIGHT BEAM, SUCH AS A LASER BEAM

(71) Applicant: FONDAZIONE ISTITUTO ITALIANO DI TECNOLOGIA, Genoa (IT)

(72) Inventors: Darwin Caldwell, Serra Riccò (IT); Leonardo De Mattos, Genoa (IT); Gianluca Pane, Ivrea (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 530 days.

(21) Appl. No.: 15/315,227

(22) PCT Filed: May 28, 2015

(86) PCT No.: PCT/IB2015/054021
§ 371 (c)(1),
(2) Date: Nov. 30, 2016

(87) PCT Pub. No.: WO2015/181771
PCT Pub. Date: Dec. 3, 2015

(65) Prior Publication Data
US 2017/0198885 A1    Jul. 13, 2017

(30) Foreign Application Priority Data
May 30, 2014 (IT) .................................. TO14A0432

(51) Int. Cl.
*G02B 7/02* (2006.01)
*G02B 26/08* (2006.01)
(Continued)

(52) U.S. Cl.
CPC .............. *F21V 14/04* (2013.01); *A61B 18/20* (2013.01); *F21V 7/0008* (2013.01);
(Continued)

(58) Field of Classification Search
CPC .......... G02B 7/02; G02B 15/14; G02B 26/08; G02B 26/10
(Continued)

(56) References Cited

U.S. PATENT DOCUMENTS 3,015,249 A    1/1962   Taylor
4,886,330 A    12/1989  Linick
(Continued)

FOREIGN PATENT DOCUMENTS

DE    10-2012-2012780 A1    1/2014
EP           1953932 A1     8/2008
(Continued)

OTHER PUBLICATIONS

International Search Report and Written Opinion from corresponding International Patent Application No. PCT/IB2015/054021, dated Sep. 22, 2015, 9 pages.

*Primary Examiner* — Dawayne Pinkney
(74) *Attorney, Agent, or Firm* — Merchant & Gould P.C.

(57) ABSTRACT

An optical orientation device includes a support structure; an optical element having an optical surface interacting with a laser beam; and a mechanism mounted on the support structure rotating the optical element around mutually perpendicular first and second fixed rotation axes. The mechanism includes a first rotary assembly articulated around a first mobile support axis, which is rotary and perpendicular relative to the first rotation axis. The first rotary assembly is coupled to the support structure to rotate around the first rotation axis, so the optical element rotates around the first rotation axis and the first mobile support axis. A second
(Continued)

rotary assembly rotates around a second mobile support axis perpendicular to the first mobile support axis. The beam passes through a cavity around the first rotation axis, the cavity facing the optical element. First and second linear actuators rotate the first rotary assembly and the second rotary assembly, respectively.

10 Claims, 6 Drawing Sheets

(51) Int. Cl.
| | |
|---|---|
| *F21V 14/04* | (2006.01) |
| *G02B 26/10* | (2006.01) |
| *G02B 7/182* | (2006.01) |
| *A61B 18/20* | (2006.01) |
| *F21V 7/00* | (2006.01) |

(52) U.S. Cl.
CPC ......... *G02B 7/1821* (2013.01); *G02B 26/101* (2013.01); *A61B 2018/2015* (2013.01)

(58) Field of Classification Search
USPC .................. 359/811–830, 694, 196.1, 197.1, 359/198.1–198.4, 210.2, 212.2, 223.1, 359/225.1, 226.1, 226.2
See application file for complete search history.

(56) References Cited

U.S. PATENT DOCUMENTS

| | | |
|---|---|---|
| 5,966,991 A | 10/1999 | Gosselin et al. |
| 2008/0037150 A1* | 2/2008 | Heuser ................ G02B 7/1824 359/874 |
| 2011/0063446 A1 | 3/2011 | McMordie et al. |

FOREIGN PATENT DOCUMENTS

| | | |
|---|---|---|
| EP | 2256397 A1 | 1/2010 |
| WO | 2007/035979 A1 | 4/2007 |

* cited by examiner

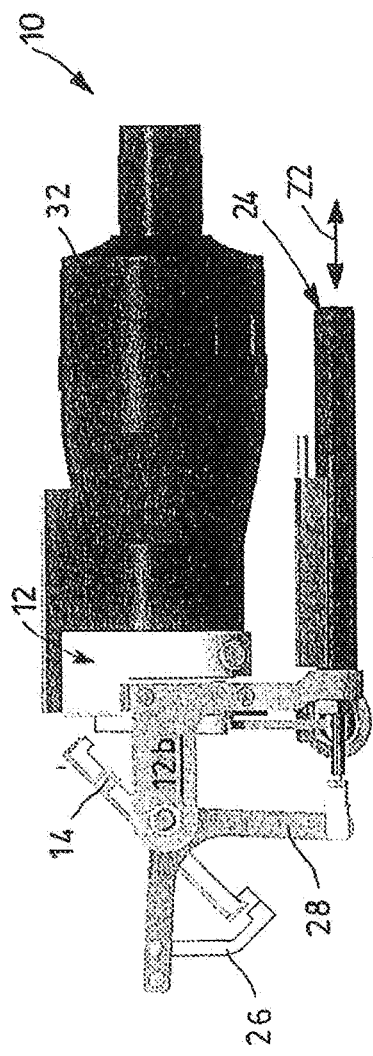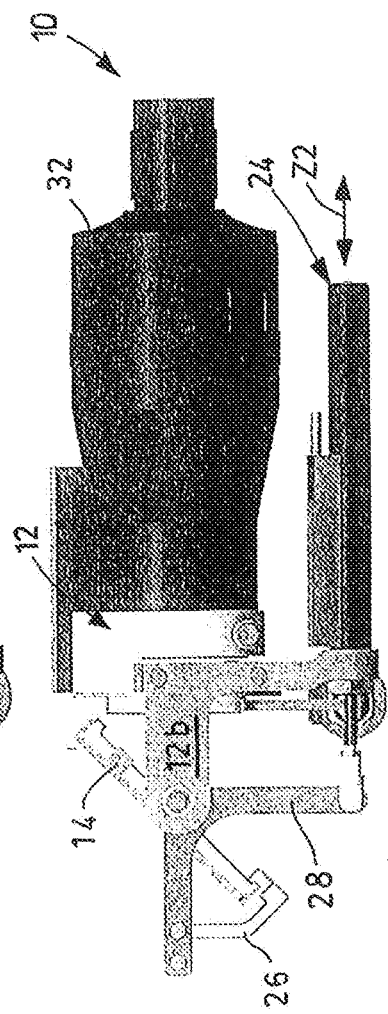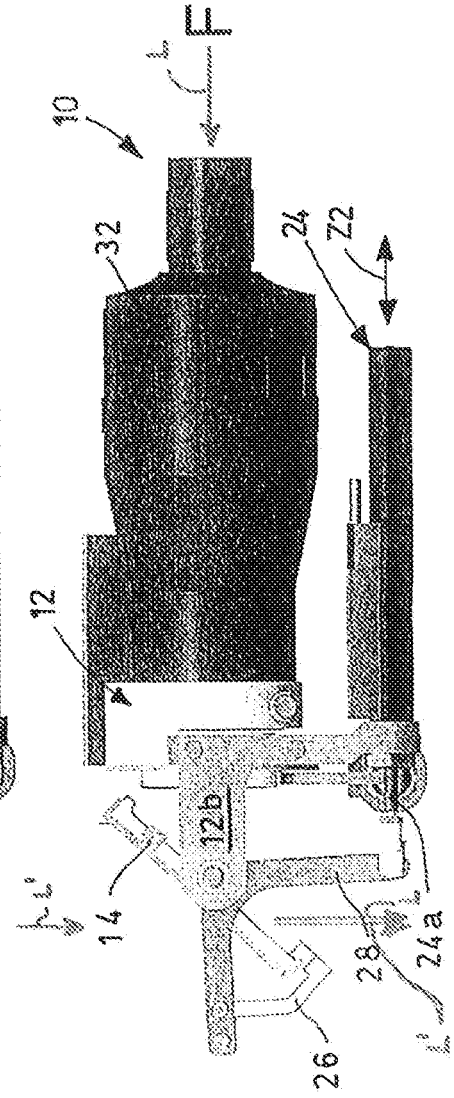

DEVICE FOR THE SPHERICAL ORIENTATION OF AN OPTICAL ELEMENT, IN PARTICULAR FOR DIRECTING A LIGHT BEAM, SUCH AS A LASER BEAM

This application is a National Stage Application of International Application No. PCT/IB2015/054021, filed 28 May 2015, which claims benefit of Ser. No. TO2014A000432, filed 30 May 2014 in Italy and which applications are incorporated herein by reference. To the extent appropriate, a claim of priority is made to each of the above disclosed applications.

TECHNICAL FIELD

The present invention relates to a device for the spherical orientation of an optical element.

TECHNOLOGICAL BACKGROUND

In technical field of reference, devices are known, which are used for the orientation of an optical element. Especially, though not exclusively, these devices can be used for the motor-driven control of the direction of a beam of light in the space.

One of the possible fields of application of these devices is—for example—that of laser (micro)surgery.

In particular, in the technical field of reference, devices of the type mentioned above are known, which are manually operated, so as to orient—in the space—a mirror that causes the light beam to converge and points it based on its position.

This type of devices is affected by numerous drawbacks, like for example that of not being provided with a motor-driven system and that of not being able to be controlled in an assisted fashion by a processor. This leads to the drawback of not being able to improve surgical quality in terms of precision and safety, thus precluding the application of some techniques, such as the automatic execution of scanning motions, of tremor filtering, of motion scaling as well as the adoption of customized control interfaces.

U.S. Pat. No. 5,966,991 discloses the use of a two degree-of-freedom spherical orienting device, which comprises a mechanism, which is operated by a pair of rotary actuators, which, in turn, are fixed to a support structure. This concept was taken up, with some changes, also in the more recent patent publication EP 2 256 397 A1.

However, the aforesaid configurations of devices using rotary motors are affected by different drawbacks.

One drawback is due to the fact that they are not suited to be used in combination with optical elements that can be passed through by a light beam (also known as see-through elements), since the mechanisms used are provided with rotary assemblies that interfere with the trajectory of the incident light beam that is suited to interact with the optical element. In particular, known mechanisms are also affected by the drawback of obstructing—or being an obstacle for—the line of sight of an observer wanting to see through the optical element (typically, from the top to the bottom or, anyway, in a direction that is substantially orthogonal to the light beam).

A further drawback results from the fact that the rotation of the motors strictly depends on the gear ration chosen. For example, for given gear ratios, the precision in the positioning of the optical element can be very high, but, in this case, it decreases the maximum reachable speed, and vice versa.

DE 10 2012 012 780 A1 describes a mirror system to deflect a laser beam. The system described therein comprises a suspension device to support the mirror, so as to allow it to rotate around two orthogonal axes, and an operating device to move the mirror. The suspension device has a first inner frame, where the mirror is held so as to be able to rotate around a first axis, and a second outer frame, where the first inner frame is held so as to be able to rotate around a second axis. The operating device is provided with two linear actuator units, each coupled in an articulated and symmetrical manner relative to the other one. The two linear actuators are arranged at a distance from one another, substantially extend in parallel directions and can be controlled separately, so as to carry out a rotation of the mirror in a desired position.

However, even the system described in the prior art document discussed above is affected by the same drawbacks mentioned above.

SUMMARY OF THE INVENTION

An object of the present invention is to provide a device, which is able to solve the aforesaid drawbacks of the prior art and which, at the same time, can be produced in a simple and economic fashion.

In particular, the device according to the present invention also allows not only the trajectory (generally oriented horizontally) of the light beam to be pointed at the optical element, but also the line of sight of an observer wanting to see through the optical element to be free and not obstructed. The line of sight typically is transverse relative to the trajectory of the light beam; in particular, in use, it is oriented from the top to the bottom or, anyway, in a direction that is substantially orthogonal to the light beam.

According to the present invention, this and other objects are reached by means of a device.

Further features and advantages of the invention will be best understood upon perusal of the following detailed description, which is provided by way of example and is not limiting, with reference, in particular, to the accompanying drawings, which are briefly described below.

BRIEF DESCRIPTION OF THE DRAWINGS

FIGS. 8-10 are views showing a moving sequence of the device shown in the previous figures, wherein a further linear actuator is operated so as to position the optical element in the space.

DETAILED DESCRIPTION OF THE INVENTION

Figure 1:
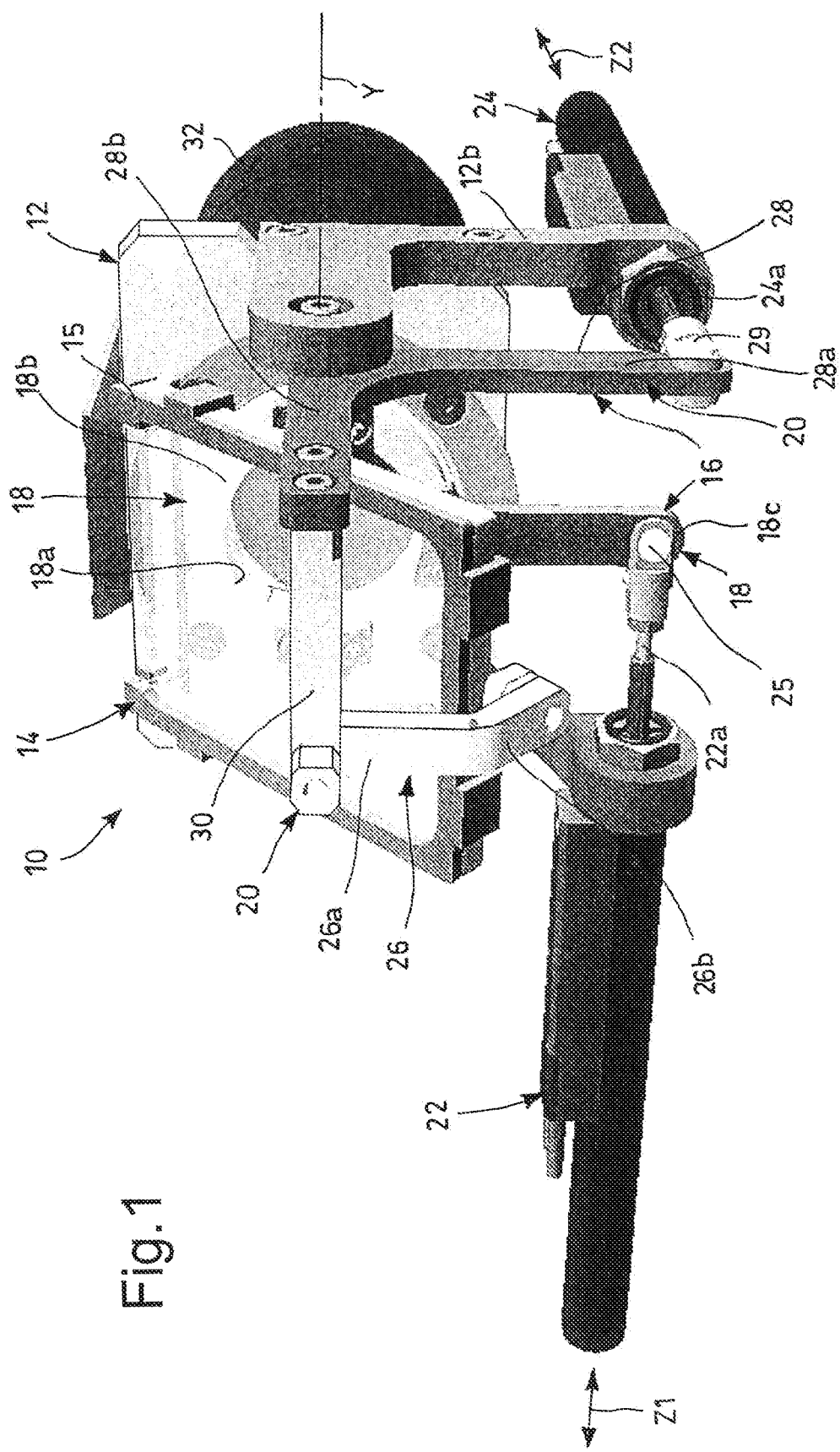
FIG. 1 is a perspective view of a device for the spherical orientation of an optical element, in particular to point a light beam, such as laser beam. The aforesaid device is manufactured according to an explanatory embodiment of the present invention and is shown from different perspectives in the same operating position.

Figures from 1 to 3 show, in different perspectives and from different angles, a device for the spherical orientation of an optical element, shown in the same operating configuration. This device is indicated, as a whole, with number 10.

In particular, device 10 is designed to be used to point a light beam, such as a laser beam. One of the possible fields of application for the aforesaid device is—for example— that of laser (micro)surgery. To this regard, device 10 can be operated so as to orient, in the desired arrangement in the space, the optical element (e.g. a mirror), which causes the beam of light L to converge and points it based on the position assumed by said optical element.

However, device 10 can also be used, more generically, to point different optical elements in different fields of application. For example, this device can be used to orient optical elements, such as sensors or lenses, in the space for different purposes.

Device 10 comprises a support structure 12 and an optical element 14 having an optically useful surface (not numbered), for interacting with an incident light beam L (e.g. a laser beam); in particular, said surface having an orientation axis O defining its position in the space. The device comprises, furthermore, a mechanism 16, which is mounted on the support structure 12 and is able to position optical element 14 by causing it to rotate around a first and a second fixed rotation axes X and Y, which are perpendicular to one another. In particular, by means of mechanism 16, the rotation of optical element 14 around the first axis X and the rotation of optical element 14 around the second axis Y can be controlled separately and independently of one another, thus granting to optical element 14 two degrees of freedom in its movements.

In this way, in the embodiment shown herein, light beam L pointed at optical element 14 is able to be direct at any point having x,y coordinates and arranged on a reference surface (for example, a surgical site in the explanatory case of laser surgery), which is faced by the optically useful surface of optical element 14.

On the one hand, mechanism 16 comprises a first rotary assembly 18, which is articulated, relative to optical element 14, around a first mobile support axis A, which is rotary and perpendicular relative to the first rotation axis X. The first rotary assembly 18, furthermore, is coupled, in a rotary manner, to support structure 12 so as to rotate around the first rotation axis X, in order to cause optical element 14 (in particular, through rotation of orientation axis O) to rotate around said first rotation axis X, and allowing said optical element 14 to rotate around the first mobile support axis A.

On the other hand, mechanism 16 comprises a second rotary assembly 20, which is articulated, relative to optical element 14, around a second mobile support axis B, which is rotary relative to the second rotation axis Y and perpendicular to the first mobile support axis A. The second rotary assembly 20, furthermore, is coupled, in a rotary manner, to support structure 12 so as to rotate around the second rotation axis Y, in order to cause optical element 14 (in particular, through rotation of orientation axis O) to rotate around the second rotation axis Y, and allowing said optical element 14 to rotate around the second support axis B.

The first rotary assembly 18 has a through cavity 18a defined around the first rotation axis X, for being passed through by a light beam (e.g. a laser beam) and faces optical element 14.

Device 10 comprises, furthermore, a first linear actuator 22 (for example an electrically operated one), for causing the first rotary assembly 18 to rotate, thus exerting upon the latter a stress (in particular, a pushing or pulling stress) in a first actuating direction Z1 that is transversely spaced apart relative to the first rotation axis X and to through cavity 18a.

Furthermore, device 10 comprises a second linear actuator 24, for causing the second rotary assembly 20 to rotate, thus exerting upon the latter a stress (in particular, a pushing or pulling stress) in a second actuating direction Z2 that is transversely spaced apart relative to the second rotation axis Y and to through cavity 18a.

In this way, device 10 is operated in a way that is quick and precise at the same time and, furthermore, the user is allowed to also use optical elements 14 that can be passed through by the light beam (also known as see-through devices). Examples of these optical elements can be a polarizer or a semi-transparent mirror or—more generically—a beam splitter.

In particular, the use of the pair of linear actuators instead of the rotary motors typically used in the prior art documents allows manufacturers to obtain a greater angular rotation speed (which, by mere way of example, can be 14 time greater) and, at the same time, a greater angular resolution (which, by mere way of example, can be 20 times greater).

Figure 2:
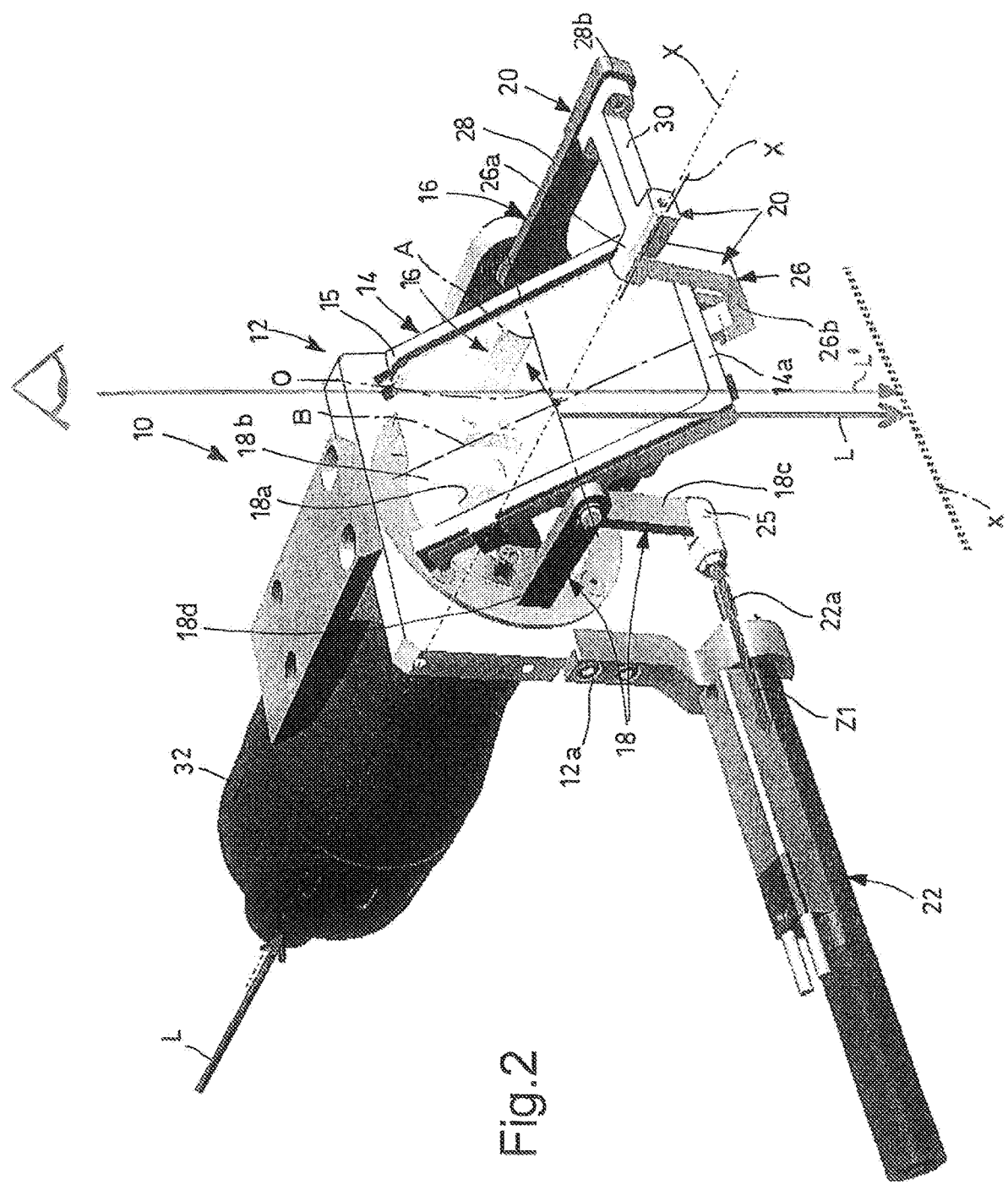
FIG. 2 is a second perspective view of a device for the spherical orientation of an optical element, in particular to point a light beam, such as laser beam. The device is manufactured according to an explanatory embodiment of the present invention and is shown from different perspectives in the same operating position.

In addition, the aforesaid configuration of device 10 does not simply free the trajectory (generally oriented horizontally) of the light beam to be pointed at optical element 14. As a matter of fact, this configuration also prevents mechanism 16 from obstructing the line of sight of an observer wanting to see through optical element 14, as shown by way of example in FIGS. 2, 3 and 10. This line of sight, indicated with L', typically is transverse and orthogonal relative to the trajectory of light beam L; in particular, in use, it is oriented from the top to the bottom. This advantage, therefore, is especially important and appreciated in case the optical element is a see-through element, for example a transparent or semi-transparent one.

Preferably, optical element 14 comprises a frame 15, which surrounds at least part of its outer perimeter.

In the embodiment shown herein, the first linear actuator 22 is fixed to support structure 12. For example, support structure 12 comprises a bracket 12a, which projects outwards and to which the first linear actuator 22 is fixed.

In the embodiment shown herein, the second linear actuator 24 is fixed to support structure 12. For example, support structure 12 comprises a further bracket 12b, which projects outwards and to which the first linear actuator 22 is fixed.

In the embodiment shown herein, the rotary coupling obtained around the second fixed rotation axis Y and arranged between the second rotary assembly 20 and support structure 12 is made in correspondence to the further bracket 12b.

In the embodiment shown herein, the first linear actuator 22 comprises a mobile member 22a, which can be moved in the first actuating direction Z1 and is able to act upon the first rotary assembly 18, so as to cause a rotation thereof around the first fixed rotation axis X. Preferably, the first actuating direction Z1 is substantially parallel to the second fixed rotation axis Y.

In the embodiment shown herein, the second linear actuator 24 comprises a mobile member 24a, which can be moved in the second actuating direction Z2 and is able to act upon said second rotary assembly 20, so as to cause a rotation thereof around the second fixed rotation axis Y. Preferably, the second actuating direction Z2 is substantially parallel to the first fixed rotation axis X.

Preferably, the first and the second actuating directions Z1 and Z2 are substantially perpendicular, in particular for an observer looking at device 10 shown in the figures from a point of observation overlooking the plan view and substantially orthogonal to the plane defined by the fixed rotation axes X, Y. In the embodiment shown herein, actuating directions Z1 and Z2 have slightly different distances relative to the plane defined by the fixed rotation axes X, Y.

In the embodiment shown herein, the first assembly 18 comprises a tubular portion 18*b*, which defines through cavity 18*a* and is housed, in a turning manner, in a substantially cylindrical seat (not numbered) obtained through support structure 12.

In the embodiment shown herein, the first assembly 18 comprises, furthermore, an arm 18*c*, which transversely projects outwards relative to the first fixed rotation axis X and is suited to be stressed (through pushing or pulling) by the first linear actuator 22.

In the embodiment shown herein, arm 18*c* transversely projects from tubular portion 18*b*, in particular from the axial end thereof.

In the embodiment shown herein, mobile member 22*a* is designed to stress (through pushing or pulling) arm 18*c*. In particular, arm 18*d* is articulated relative to the first mobile member 22*a*, for example through the interposition of a first articulation indicated, as a whole, with number 25. Advantageously, though not necessarily, mobile member 22*a* is hinged, relative to arm 18*d*, around a first mobile hinge axis (not numbered), which, for example, is parallel to and spaced apart from the first rotations axis X.

In the embodiment shown herein, the first assembly 18 comprises a pair of axial appendages 18*d*, which axially project outwards and on which optical element 14 is articulated—and preferably hinged—around the first mobile support axis A. In particular, the pair of axial appendages 18*d* extend on diametrically opposite sides of tubular portion 18*b*. For example, the axial appendages 18*d* comprise a pair of L-shaped brackets, which are fixed (for example screwed) at their base to tubular portion 18*b*.

Preferably, optical element 18 is articulated—and in particular hinged—to the first rotary assembly 18 in correspondence to frame 15.

In an alternative embodiment (not shown herein), the first assembly can comprise one single axial appendage, which axially projects outwards and on which the optical element is articulated—and preferably hinged—around the first mobile support axis.

In the embodiment shown herein, the second rotary assembly 20 is articulated to a peripheral portion 14*a* of optical element 14 (for example, in correspondence to a peripheral edge of the optical element) around the second mobile support axis B. Advantageously, though not necessarily, peripheral portion 14*a* is arranged in an intermediate part of the peripheral edge of optical element 14.

Preferably, the aforesaid peripheral portion 14*a* can be placed along frame 15.

Figure 3:
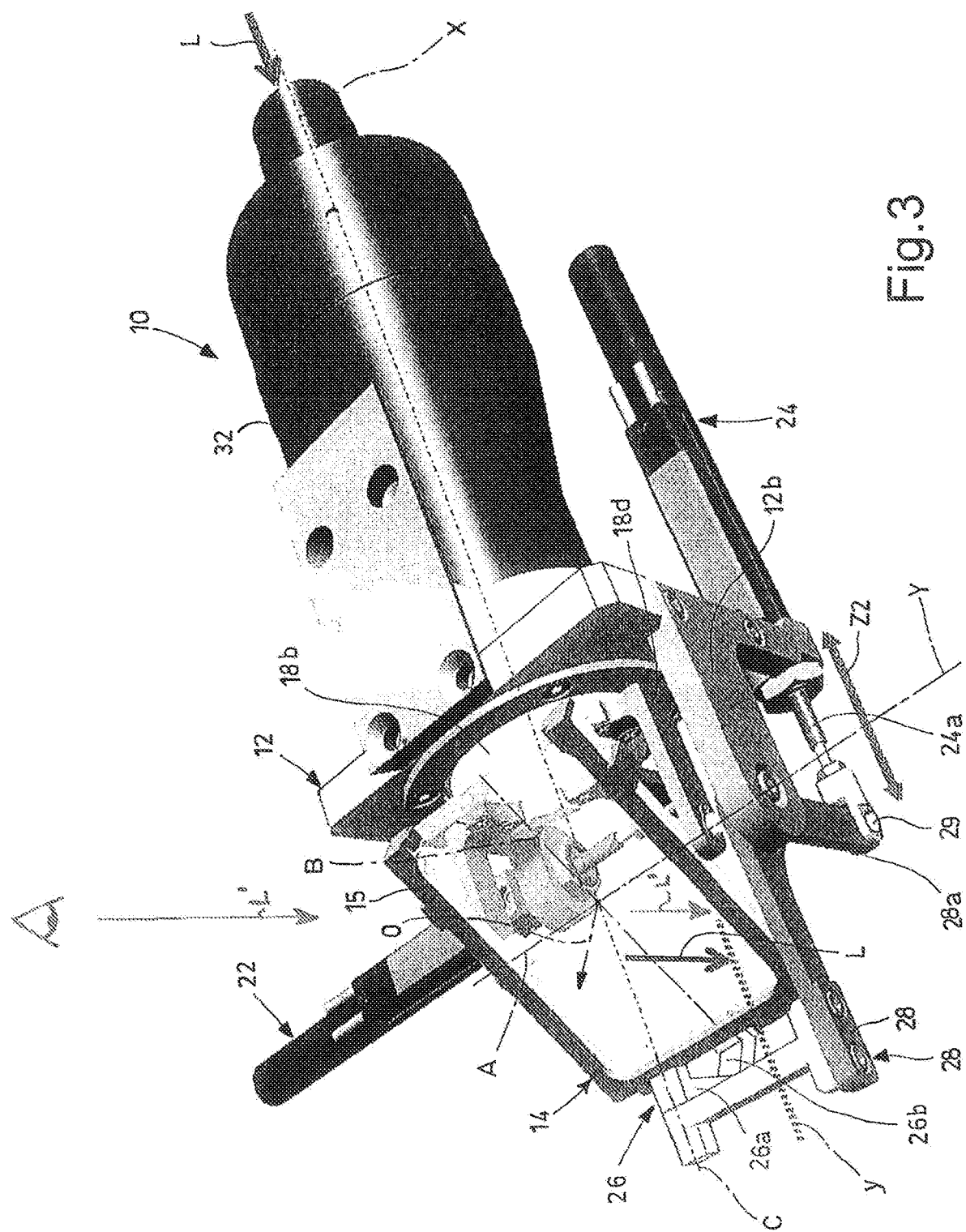
FIG. 3 is a third perspective view of a device for the spherical orientation of an optical element, in particular to point a light beam, such as laser beam. The device is manufactured according to an explanatory embodiment of the present invention and is shown from different perspectives in the same operating position.
Figure 4:
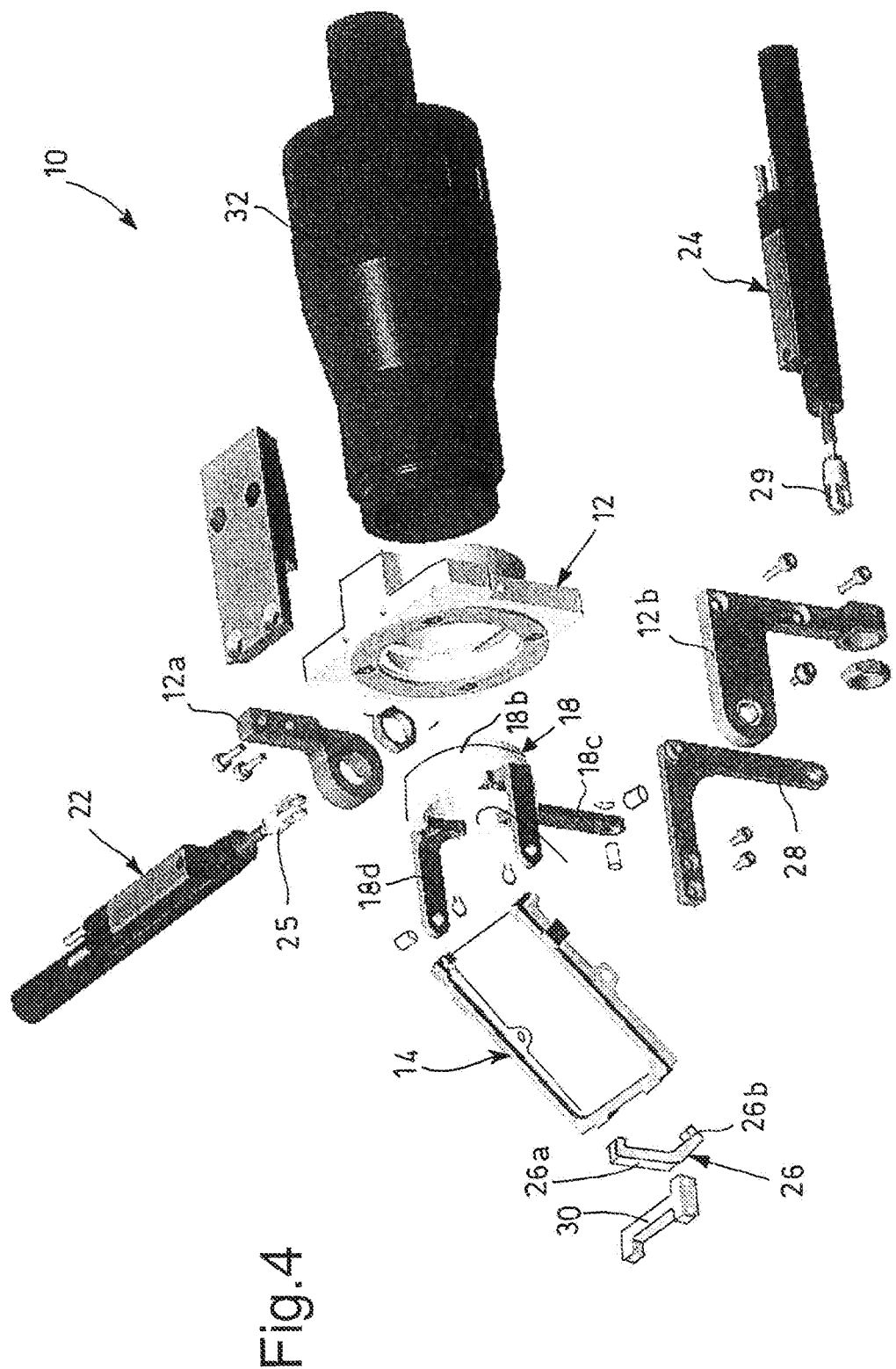
FIG. 4 is an exploded view of the device shown in the previous figures.
Figure 5:
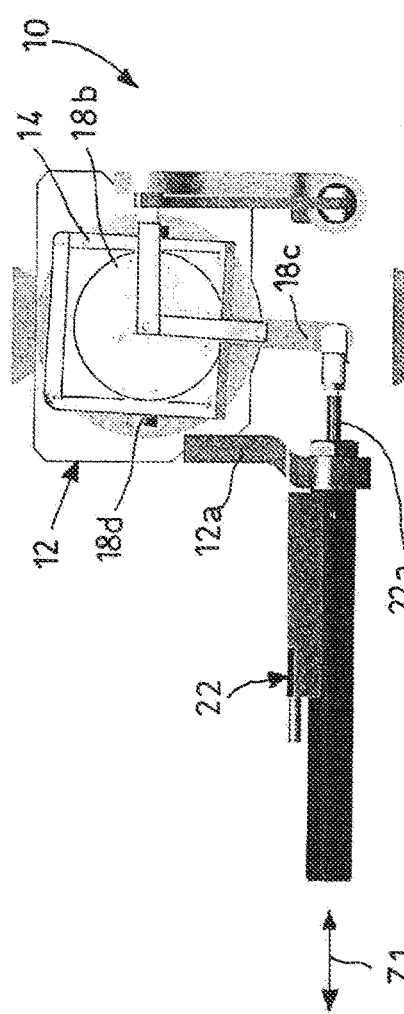
FIGS. 5-7 are front views showing a moving sequence of the device shown in the previous figures, wherein a linear actuator is operated so as to position the optical element in the space.
Figure 6:
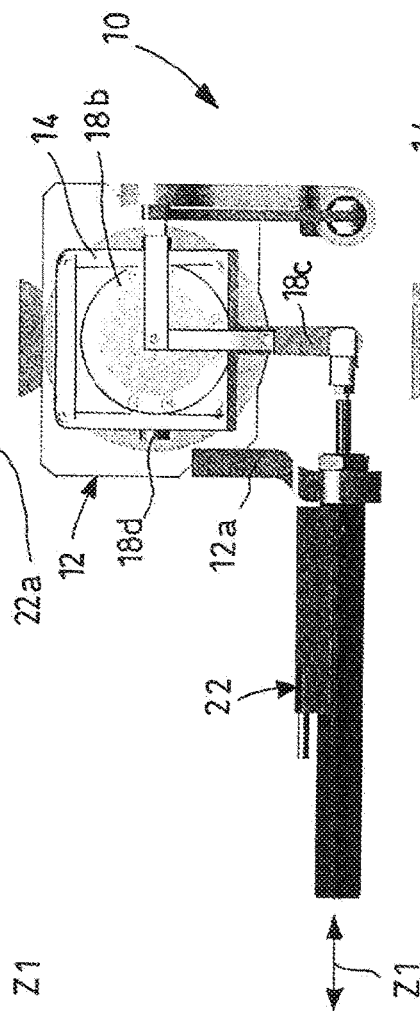
Figure 7:
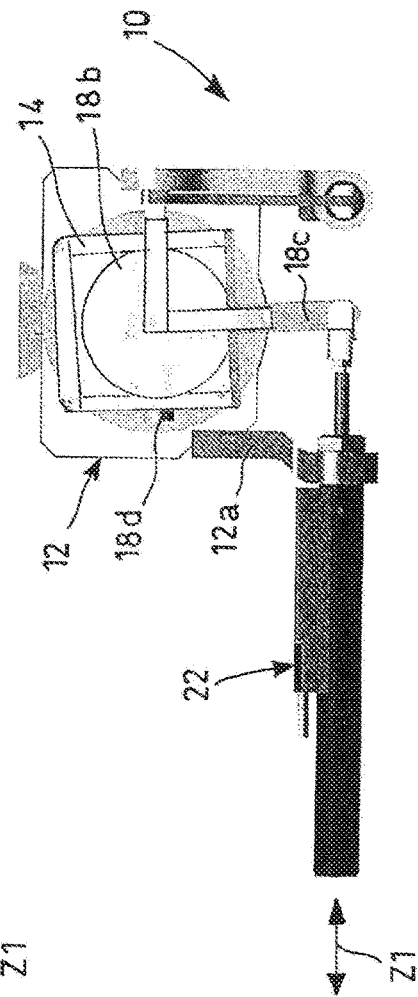

In the embodiment shown herein, the second rotary assembly 20 comprises a connecting segment 26, which, on one side, is articulated (and in particular hinged), relative to said optical element 14, around said second mobile support axis B and, on the other side, is articulated (and in particular hinged), relative to the rest of rotary assembly 20, around a mobile articulation axis C, which is rotary and perpendicular relative to the second rotation axis Y. In particular, mobile articulation axis C passes through the intersection between the fixed rotation axes X and Y. In FIGS. 1 and 3, device 10 is shown in a configuration in which mobile articulation axis C is in a position that is substantially coaxial to the first fixed rotation axis X, but this axis can move and rotate around the second fixed rotation axis Y, upwards or downwards relative to the aforesaid first fixed rotation axis X.

In the embodiment shown herein, connecting segment 26 is preferably articulated (and in particular hinged) to peripheral portion 14*a* around support axis B.

In the embodiment shown herein, the second assembly 20 comprises a lever 28, which is mounted on support structure 12 so as to rotate around the second fixed rotation axis Y. Preferably, lever 28 is a rocker arm and, more preferably, it is substantially L-shaped and it is pivoted around the second rotation axis Y in correspondence to the intersection between its two lever arms 28*a*, 28*b*.

In particular, lever 28 is supported, during its rotation, by support structure 12 in correspondence to the further bracket 12*b*.

In the embodiment shown herein, rocker arm 28 has a lever arm 28*a*, which is suited to be stressed (through pushing or pulling) by the second linear actuator 24, and the other lever arm 28*b* is suited to impart a rotation towards optical element 14.

Preferably, the second mobile member 24*a* is suited to stress (through pushing or pulling) lever arm 28*a*. In particular, lever arm 28*a* is articulated relative to the second mobile member 24*a*, for example through the interposition of a second articulation indicated, as a whole, with number 29. Advantageously, though not necessarily, the second mobile member 24*a* is hinged, relative to lever arm 21*d*, around a second mobile hinge axis (not numbered), which, for example, is parallel to and spaced apart from the second rotations axis Y.

In the embodiment shown herein, lever arm 28*a* and the the other lever arm 28*b* substantially lie on a plane that is perpendicular to the rotation axis Y.

In the embodiment shown herein, the second rotary assembly 20 comprises a transverse segment 30, which is connected to lever 28 and substantially departs transversely from said lever 28 towards the first fixed rotation axis X. In particular, transverse segment 30 extends substantially parallel to the second fixed rotation axis X.

In the embodiment shown herein, transverse segment 30 departs from lever 28 in correspondence to the other lever arm 28*b*, in particular in correspondence to the latter.

In the embodiment shown herein, connecting segment 26 is articulated—in particular hinged—to transverse segment 30 around intermediate articulation axis C.

In the embodiment shown herein, connecting segment 26 has a shape that is substantially bent towards optical element 14.

Preferably, connecting segment 26 comprises a proximal portion 26*a*, which departs from transverse segment 30 in a direction that is substantially perpendicular relative to mobile articulation axis C. Furthermore, connecting segment 26 also comprises a distal portion 26*b*, which is inclined at approximately 45° towards optical element 14 relative to the direction of proximal portion 40*a*.

In the embodiment shown herein, distal portion 26*b* is articulated—in particular hinged—to optical element 14 around the second support axis B, on the opposite side relative to proximal portion 26*a*.

Preferably, distal portion 26b is articulated—in particular hinged—to peripheral portion 14a of optical element 14 around the second support axis B.

In the embodiment shown herein, device 10 comprises, furthermore, a known light beam generator 32, for emitting the light beam, pointing it through cavity 18a. For example, light beam generator 32 is fixed to support structure 12 in a position that is aligned relative to through cavity 18a and, in particular, coaxial to the first fixed rotation axis X.

In the embodiment, optical element 14 is a mirror, for reflecting incident light beam L towards the point of intersection of support axes A and B, corresponding to its center of rotation (in particular, from which orientation axis O departs perpendicularly). In particular, said mirror is flat, for example with a substantially rectangular shape.

With reference, in particular, to figures from 5 to 10, one can see two explanatory moving sequences, which the device can follow through the operation of the first linear actuator 22 and of the second linear actuator 24, respectively.

In the embodiment shown herein (as one can see in particular in the sequence shown in figures from 5 to 7), when the first linear actuator 22 is operated, the first mobile member 22a is translated along the first actuating direction Z1. In this way, the first mobile member 22a stresses arm 18c, by pushing or pulling it, which causes the simultaneous rotation of tubular portion 18b around the first fixed rotation axis X. Consequently, axial appendages 18d rotate in an integral manner with said tubular portion 18b, thus rotating with them (around the first fixed rotation axis X) the first support axis A, on which optical element 14 is hinged. Therefore, by so doing, incident light beam L can be pointed at optical element 14 moving it along an axis x (see FIG. 2).

In the embodiment shown herein (as one can see in particular in the sequence shown in figures from 8 to 10), when the second linear actuator 24 is operated, the second mobile member 24a is translated along the second actuating direction Z2. In this way, the second mobile member 24a stresses lever arm 28a, by pushing or pulling it, which causes the simultaneous rotation of lever 28 around the second fixed rotation axis Y. Consequently, transverse segment 30 and connecting segment 26 are rotated in the same direction around the second rotation axis Y. In this way, connecting segment 26 tends to rotate (around the second fixed rotation axis Y) the second support axis B, on which optical element 14 is articulated. Therefore, by so doing, incident light beam L can be pointed at optical element 14 moving it along an axis y (see FIG. 3).

As a person skilled in the art can easily understand, the first actuator 22 and the second actuator 24 can be operated at the same time, so that they can move optical element 14 in the space.

In the embodiment shown herein, the optional assembling of connecting segment 26 relative to the rest of the second rotary assembly 20, thanks to the freedom of rotation relative to mobile hinge axis C, permits the simultaneous operation of linear actuators 22 and 24, without any interference with the movements of rotary assemblies 18 and 20 of mechanism 16.

Naturally, the principle of the present invention being set forth, embodiments and implementation details can be widely changed relative to what described above and shown in the drawings as a mere way of non-limiting example, without in this way going beyond the scope of protection provided by the accompanying claims.

The invention claimed is:

1. A device for spherical orientation of an optical element; said device comprising:
   a support structure,
   an optical element having an optically useful surface for interacting with an incident laser beam, said optical element comprising a transparent or semi-transparent element, and
   a mechanism, which is mounted on said support structure and rotates said optical element in a space around a first fixed rotation axis and a second fixed rotation axis, which are perpendicular to one another; said mechanism comprising:
   a first rotary assembly, which is articulated, relative to said optical element, around a first mobile support axis, which is rotary and perpendicular relative to the first rotation axis, said first rotary assembly being rotatably coupled to the support structure so as to rotate around the first rotation axis, in order to rotate the optical element around said first rotation axis, and allowing said optical element to rotate around said first mobile support axis; wherein said first rotary assembly has a through cavity defined around said first rotation axis passed through by said laser beam and facing said optical element; said optical element being passed through by a line of sight of an observer, the line of sight of the observer being substantially oriented orthogonal relative to a trajectory of said beam of light;
   a second rotary assembly, which is articulated, relative to said optical element, around a second mobile support axis, which is rotary relative to said second rotation axis and perpendicular to said first mobile support axis, said second rotary assembly being rotationally coupled to the support structure so as to rotate around said second rotation axis, in order to rotate said optical element around said second rotation axis, and allowing said optical element to rotate around said second support axis;
   a first linear actuator, which rotates said first rotary assembly, thus exerting upon the first rotary assembly a stress in a first actuating direction that is transversely spaced apart relative to said first rotation axis and to said through cavity; and
   a second linear actuator, for causing said second rotary assembly to rotate, thus exerting upon the second rotary assembly a stress in a second actuating direction that is spaced apart relative to the second rotation axis and to the through cavity;
   wherein the line of sight of the observer is unobstructed by the mechanism.

2. The device according to claim 1, wherein said first linear actuator comprises a mobile member, which can be moved in the first actuating direction and is able to act upon the first rotary assembly, so as to cause a rotation of said first rotary assembly around said first fixed rotation axis.

3. The device according to claim 1, wherein said first actuating direction is substantially parallel to the second fixed rotation axis.

4. The device according to claim 1, wherein said second linear actuator comprises a mobile member, which can be moved in the second actuating direction and is able to act upon said second rotary assembly, so as to cause a rotation of said second rotary assembly around said second fixed rotation axis.

5. The device according to claim 1, wherein said second actuating direction is substantially parallel to said first fixed rotation axis.

6. The device according to claim 1, wherein said first and second actuating directions are substantially perpendicular.

7. The device according to claim 1, wherein said first assembly comprises a tubular portion, which defines said through cavity and turns and is housed in a substantially cylindrical seat obtained through said support structure.

8. The device according to claim 1, wherein said first assembly further comprises an arm, which transversely projects outwards relative to said first fixed rotation axis and is stressed by said first linear actuator.

9. The device according to claim 1, wherein said second rotary assembly is articulated to a peripheral portion of said optical element around said second mobile support axis.

10. The device according to claim 1, wherein said second rotary assembly comprises a connecting segment, which, on one side, is articulated, relative to said optical element, around said second mobile support axis and, on the other side, is articulated, relative to a rest of said rotary assembly, around a mobile articulation axis, which is rotary and perpendicular relative to said second rotation axis.

* * * * *

UNITED STATES PATENT AND TRADEMARK OFFICE
CERTIFICATE OF CORRECTION

PATENT NO. : 10,738,973 B2
APPLICATION NO. : 15/315227
DATED : August 11, 2020
INVENTOR(S) : Caldwell et al.

Page 1 of 1

It is certified that error appears in the above-identified patent and that said Letters Patent is hereby corrected as shown below:

On the Title Page

(30) Foreign Application Priority Data: "May 30, 2014 (IT) TO14A0432" should read --May 30, 2014 (IT) TO2014A000432--

Signed and Sealed this
Twenty-ninth Day of December, 2020

Andrei Iancu
*Director of the United States Patent and Trademark Office*